United States Patent [19]

Simard et al.

[11] Patent Number: 5,895,578
[45] Date of Patent: Apr. 20, 1999

[54] METHOD OF DISINFECTION FOR A DIALYSIS MACHINE

[75] Inventors: Laurent Simard, Saint Genis Laval, France; Renato Pedrazzi, Mirandola Modena, Italy

[73] Assignee: Hospal Industrie, Meyzieu, France

[21] Appl. No.: 08/874,324

[22] Filed: Jun. 13, 1997

[30] Foreign Application Priority Data

Jun. 18, 1996 [FR] France ................... 96 07822

[51] Int. Cl.$^6$ ................... A61L 2/16; A61L 2/18
[52] U.S. Cl. ................... 210/636; 134/22.1; 134/22.11; 210/32.169; 422/28; 422/37
[58] Field of Search ................... 210/636, 501, 210/321.69, 646; 422/28, 37; 134/22.1, 22.11

[56] References Cited

U.S. PATENT DOCUMENTS

| | | | |
|---|---|---|---|
| 4,332,264 | 6/1982 | Gortz et al. | 210/321.69 |
| 4,399,030 | 8/1983 | Hlavinka et al. | 210/91 |
| 4,695,385 | 9/1987 | Boag | 210/636 |
| 4,789,467 | 12/1988 | Lindsay et al. | 210/321.69 |
| 5,178,830 | 1/1993 | Riera Aixala | 422/37 |
| 5,244,568 | 9/1993 | Lindsay et al. | 210/321.69 |
| 5,336,165 | 8/1994 | Twardowski | 210/636 |
| 5,409,612 | 4/1995 | Maltais et al. | 210/636 |
| 5,453,245 | 9/1995 | Kirschner et al. | 422/28 |
| 5,702,597 | 12/1997 | Chevallet et al. | 210/321.69 |

FOREIGN PATENT DOCUMENTS 0 403 401  3/1994  European Pat. Off.
0 694 312  1/1996  European Pat. Off.

*Primary Examiner*—John Kim
*Attorney, Agent, or Firm*—Finnegan, Henderson, Farabow, Garrett & Dunner, L.L.P.

[57] ABSTRACT

A method for disinfection of the hydraulic circuit of a dialysis machine, comprising an inlet (E) for connection to an external water source and a plurality of open lines (1, 2, 4a, 4b, 26) intended to be connected, in an operational configuration of the machine, to different consumable accessories, comprises the steps of:

closing the open lines on the hydraulic circuit in such a way as to form a closed network of lines;

bringing a reservoir (40) containing a concentrated disinfection liquid into communication with the hydraulic circuit, in proximity to the inlet;

instigating a proportional flow of water and of concentrated disinfection liquid in the hydraulic circuit in such a way as to produce a first liquid having a bactericidal action;

interrupting the flow of water and of concentrated disinfection liquid when the hydraulic circuit is filled with bactericidal liquid, the initial volume of concentrated disinfection liquid in the reservoir being chosen such that at the end of the filling of the hydraulic circuit, a residual volume remains in the reservoir (40);

adding a volume of water to the residual volume in the reservoir (40) in order to produce a second liquid;

emptying the hydraulic circuit of the bactericidal liquid;

instigating simultaneously a proportional flow of water and of the second liquid in the hydraulic circuit in such a way as to produce a third liquid having a bacteriostatic action and capable of remaining in the hydraulic circuit for at least twelve hours without causing corrosion there;

filling the hydraulic circuit with bacteriostatic liquid.

14 Claims, 1 Drawing Sheet

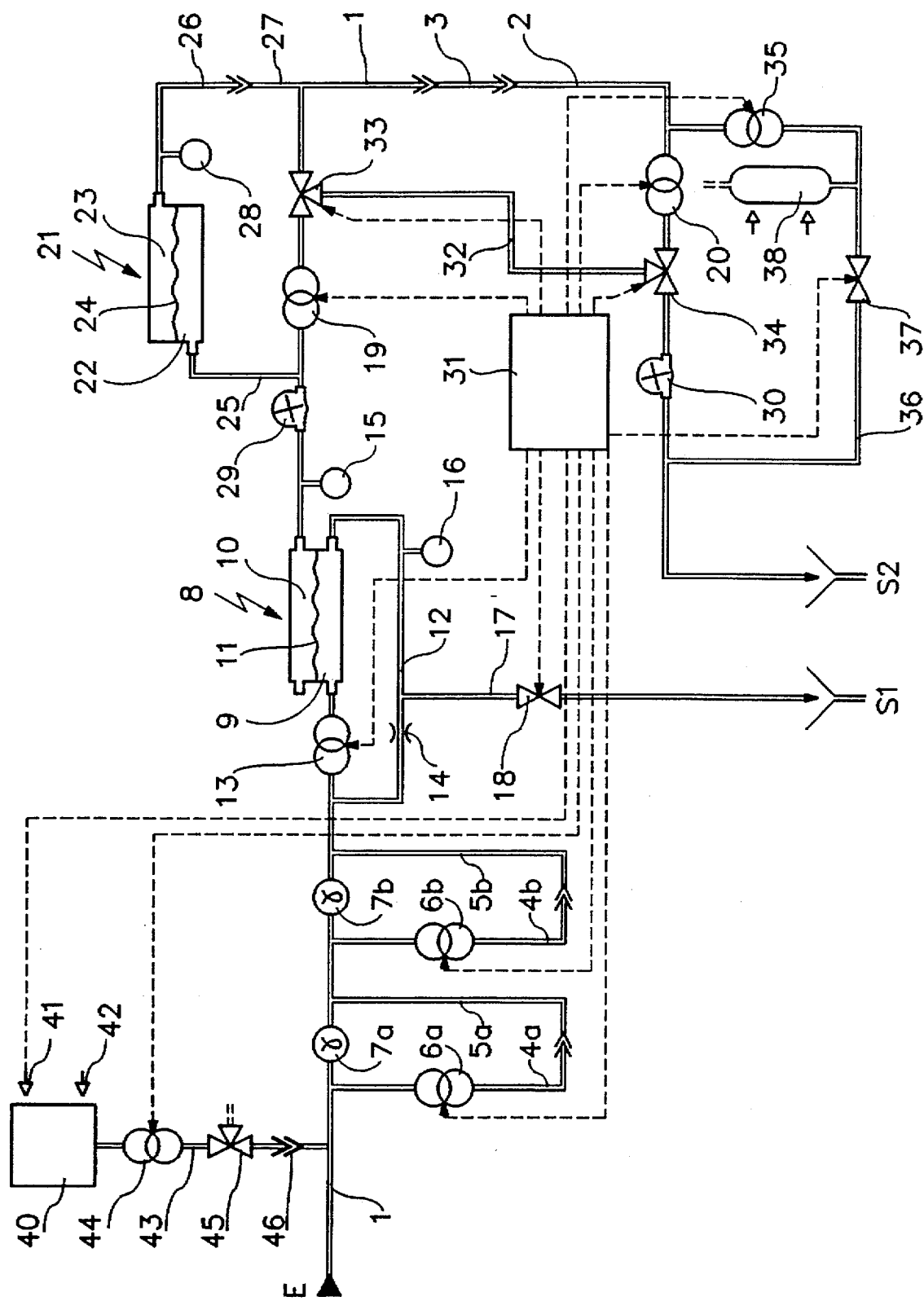

METHOD OF DISINFECTION FOR A DIALYSIS MACHINE

BACKGROUND OF THE INVENTION

1. Field of the Invention

The present invention relates to a disinfection method for a dialysis machine.

2. Description of the Related Art

The principal functions of a dialysis machine are preparing a dialysis liquid, supplying dialysis liquid to a dialyser, and removing the used liquid (mixture of dialysis liquid charged with the waste products of metabolism and plasma water) from the dialyser.

The dialysis liquid is prepared by a metered mixing of water and two concentrated solutions containing the principal electrolytes of blood. The mixture is maintained at a substantially constant temperature by heating the water, and, in some machines, it is filtered in such a way that the liquid circulating in the dialyser is free from microorganisms and pyrogenic elements. The fresh filtered dialysis liquid can be filtered a second time to serve as perfusion liquid.

A dialysis machine comprises a hydraulic circuit consisting of an assembly of lines, pumps, valves, filters, etc., which are susceptible to clogging, which is likely to favour the development of undesirable bacterial flora. It is expedient to filter the dialysis liquid, because even if the blood in a dialyser is isolated from the dialysis liquid by a semipermeable membrane which in principle does not allow the bacteria to pass through, contamination of the blood is still possible in the event of microscopic leakages in the membrane. In addition, the bacterial derivatives of low molecular weight can pass through the membranes of the dialysers.

The zones of the machine which are the most prone to clogging are the filters which are used to filter the dialysis liquid, and in the first chamber of which all the materials stopped by the membrane of these filters are concentrated, as well as the whole circuit for removal of the used liquid which is in contact with organic substances (waste products of metabolism, plasma water).

The present-day dialysis machines are therefore equipped with a disinfection system which makes it possible to fill the hydraulic circuit with a disinfection liquid, then to purge it of this liquid, after the disinfectant has stagnated therein for a defined period of time. The hydraulic circuit is then flushed with water and remains filled with water until the machine is next used. In general, the machines are disinfected between two dialysis sessions. After the final dialysis session of the day, depending on the type of disinfectant used, the machines either remain filled with disinfection liquid for the night, or they are flushed with water after disinfection and remain filled with water for the night. The difference in treatment stems from the fact that some disinfectants (for example chlorine-based disinfectants) are corrosive and their prolonged stagnation in the machine would damage its hydraulic circuit.

There is a drawback to leaving the machines filled with water for several hours: if the disinfection has not eliminated all the microorganisms present in the hydraulic circuit, the surviving microorganisms will be able to multiply and colonize some zones of the circuit where the disinfection action is less effective.

On the other hand, the chlorine-based disinfectants, such as Javelle water, are reputed to be the most effective, and they have an additional effect of cleaning the circuit (organic deposits), an effect not possessed by the other disinfectants currently used (aldehyde-based disinfectants, and disinfectants based on peracetic acid).

SUMMARY OF THE INVENTION

An object of the invention is to provide a disinfection system for a dialysis machine, which system permits the use of corrosive disinfectants without such use resulting in damage to the hydraulic circuit of the machine, nor its possible colonization by microorganisms during the periods of prolonged inactivity of the machine.

To achieve this object, the invention provides a method for disinfection of the hydraulic circuit of a dialysis machine, comprising an inlet for connection to an external water source and a plurality of open lines intended to be connected, in an operational configuration of the machine, to different consumable accessories, comprising the steps of:

closing the open lines on the hydraulic circuit in such a way as to form a closed network of lines;

bringing a reservoir containing a concentrated disinfection liquid into communication with the hydraulic circuit, in proximity to the inlet;

instigating a proportional flow of water and of concentrated disinfection liquid in the hydraulic circuit in such a way as to produce a first liquid having a bactericidal action; characterized in that it comprises the steps of:

interrupting the flow of water and of concentrated disinfection liquid when the hydraulic circuit is filled with bactericidal liquid, the initial volume of concentrated disinfection liquid in the reservoir being chosen such that at the end of the filling of the hydraulic circuit, a residual volume remains in the reservoir;

adding a volume of water to the residual volume in the reservoir in order to produce a second liquid;

emptying the hydraulic circuit of the bactericidal liquid;

instigating simultaneously a proportional flow of water and of the second liquid in the hydraulic circuit in such a way as to produce a third liquid having a bacteriostatic action and capable of remaining in the hydraulic circuit for at least twelve hours without causing corrosion there; and filling the hydraulic circuit with bacteriostatic liquid.

By virtue of this method, it is possible to use a corrosive disinfectant to disinfect a dialysis machine without having to leave the hydraulic circuit filled with water between two treatment sessions separated by several hours. The stagnation of a bacteriostatic liquid prevents the formation of a biofilm in the hydraulic circuit. Another advantage of this method is that it is simple to implement and that it affords complete safety since it is based on the use of a bactericidal liquid and a bacteriostatic liquid of the same chemical nature, the accidental mixing of which liquids would of course not cause any undesired reaction (as might be the case if these two liquids were of different chemical natures).

According to one characteristic of the invention, prior to the step of bringing the reservoir into communication with the hydraulic circuit, the method comprises the step of filling the reservoir with a defined volume of concentrated disinfection liquid.

According to another characteristic of the invention, prior to the step of bringing the reservoir into communication with the hydraulic circuit, the method comprises the step of filling the reservoir with a defined volume of water and of introducing thereto a defined quantity of soluble disinfectant in the form of a powder, granules or pellets.

According to yet another characteristic of the invention, the step of filling the hydraulic circuit with the bactericidal liquid and the step of filling the hydraulic circuit with the bacteriostatic liquid are performed in several phases corresponding to the filling of several portions of the hydraulic circuit.

Other characteristics and advantages of the invention will become evident from reading the description which follows.

BRIEF DESCRIPTION OF THE FIGURE

Reference will be made to the attached drawing in which the single FIGURE represents the flow diagram of a dialysis machine in which the hydraulic circuit is arranged in a non-operational configuration (disinfection configuration).

DETAILED DESCRIPTION OF THE PREFERRED EMBODIMENT

For reasons of clarity, the FIGURE does not show some of the elements and accessories with which traditional dialysis machines are equipped and whose representation and description would not help in understanding the invention (such as, for example, a pressure regulator for the water intake, a device for heating the water, devices for degassing the water and the dialysis liquid, a heat exchanger, etc.).

The dialysis machine represented in the FIGURE comprises a control unit and a hydraulic circuit which is arranged in a non-operational configuration (as opposed to an operational configuration permitting treatment administration).

The hydraulic circuit comprises a supply line 1 which supplies fresh dialysis liquid and which is intended to connect a dialysis liquid generator to an inlet of a haemodialyser, and a removal line 2 which removes used liquid and which is intended to connect an outlet of a haemodialyser to the drainage system. As the machine is in the non-operational configuration, the supply line 1 and the removal line 2 are connected via a junction line 3 whose ends are equipped with connector elements identical to those of a haemodialyser.

The dialysis liquid generator comprises a first device for mixing a first concentrated solution with water coming from a source external to the machine (branch provided at the inlet E, at the upstream end of the supply line 1), and a second device for mixing a second concentrated solution with the diluted solution produced by the first mixing device. Each mixing device comprises an injection line 4a, 4b having one end connected to the supply line 1 and one end equipped with a connector for connecting the injection line 4a, 4b either to a source of concentrated solution (operational configuration) or to a loop line 5a, 5b (non-operational configuration). The injection line 4a, 4b is equipped with a metering pump 6a, 6b whose delivery rate is controlled as a function of information supplied via a conductivity probe 7a, 7b arranged on the supply line 1, downstream of the junction of the injection line 4a, 4b to the supply line 1.

The hydraulic circuit additionally comprises a first filter 8 for filtering the dialysis liquid produced by the dialysis liquid generator. The filter 8 has a first and a second chamber 9, 10 which are separated by a filtration membrane 11, the first chamber 9 having an inlet connected to a first portion of the supply line 1, and the second chamber 10 having an outlet connected to a second portion of the supply line 1. A recirculation line 12 connects an outlet of the first chamber 9 of the filter 8 to the inlet of this first chamber. On this recirculation line 12 there are a scavenging pump 13, immediately upstream of the first chamber 9 of the filter 8, and a constriction member 14, which is optionally controllable.

Two pressure sensors 15, 16 are arranged on the supply line 1 and on the recirculation line 12, respectively, at the outlet of the first and second chambers 9, 10 of the filter 8.

A purge line 17 of the first chamber 9 of the filter 8, on which line a valve 18 is arranged, is connected to the recirculation line 12 between the outlet of the first chamber 9 of the filter 8 and the constriction member 14. The purge line 17 is connected to the drainage system via a first outlet S1 of the dialysis machine distinct from a second outlet S2 which forms the end of the removal line 2 for the used liquid.

The dialysis liquid is circulated in the hydraulic circuit by means of a first pump 19 arranged on the supply line 1, downstream of the filter 8, and by means of a second pump 20 arranged on the removal line 2.

The hydraulic circuit additionally includes a perfusion liquid generator comprising a second filter 21 which has a first chamber 22 and a second chamber 23 which are separated by a filtration membrane 24. The first chamber 22 has an inlet connected via a line 25 to the supply line 1, between the first filter 8 and the first pump 19 for circulating the dialysis liquid. The second chamber 23 has an outlet connected to a perfusion line 26 whose free end is equipped with a connector for connecting the perfusion line 26 either to a loop line 27 connected to the supply line 1 (non-operational configuration), or to a line connected to a bubble trap of a circuit for the extracorporeal circulation of blood (operational configuration). A pressure sensor 28 is arranged on the perfusion line 26.

The hydraulic circuit also comprises a system for volumetric control of the ultrafiltration, comprising a first flow meter 29, arranged on the supply line 1 between the first filter 8 and the first circulation pump 19, and a second flow meter 30, arranged on the removal line 2 downstream of the second circulation pump 20. The measurements made by the two flow meters are compared by the computing and control unit 31 which governs the second circulation pump 20 in such a way that the flow rates measured by the two flow meters are identical. A calibration line 32 connects the supply line 1 to the removal line 2 by way of two three-way valves 33, 34 arranged on the one hand downstream of the first circulation pump 19 and on the other hand between the second circulation pump 20 and the second flow meter 30. An ultrafiltration pump 35 is arranged on a branch line 36 branching from the removal line 2, the upstream end of the branch line 36 being connected to the removal line 2 upstream of the second pump 20, and the downstream end of the branch line 36 being connected to the removal line 2 downstream of the second flow meter 30. A device for measuring the delivery rate of the ultrafiltration pump 35, comprising a valve 37 and a burette 38 equipped with two level detectors, is arranged on the branch line 36 downstream of the ultrafiltration pump 35. This device for measuring the delivery rate is described in detail in the document EP 0 403 401.

The hydraulic circuit finally includes a disinfection device comprising a reservoir 40 equipped with an upper level detector 41 and a bottom level detector 42. A line 43 connects the base of the reservoir 40 to the supply line 1 upstream of the dialysis liquid generator, in proximity to the inlet orifice E of the machine. This line is equipped (in the order starting from the reservoir 40) with a pump 44, a three-way valve 45 permitting communication between the reservoir 40 and the burette 38 by way of a line which is not shown, and a connector 46 by means of which it is possible to connect the reservoir 40 to a source of liquid, in particular to a source of water or of concentrated disinfection liquid.

The computing and control unit 31 is connected to all the measurement instruments of the hydraulic circuit which has just been described (conductivity probes, pressure sensors, flow meters, level detectors, etc.). In addition, it is connected to all the pumps and valves and controls their flow rates, opening and closure as a function of reference values, measurements carried out by the measurement instruments, programs describing all the operational cycles of the machine, in particular the disinfection cycle according to the invention.

In accordance with the invention, the preparation of the machine with a view to a prolonged non-operational state is carried out in the following way. At the end of a treatment session, which takes place in accordance with the description given in the document EP 0 694 312, all the open lines of the hydraulic circuit, that is to say the lines having one end connected to a consumable accessory, are looped back to the hydraulic circuit by means of the loop lines or junction lines provided for this purpose (lines 4a, 4b for injection of concentrated solutions used for preparing the dialysis liquid; perfusion line 26; supply line 1 and removal line 2). The lines 4a, 4b, 26 are thus looped back to the hydraulic circuit by means of the loop lines 5a, 5b, 27, and the lines 1 and 2 connected via the junction line 3.

The hydraulic circuit thus forms a closed network of lines having an inlet E for the water and the two outlets S1, S2 described above. It is filled on the one hand with fresh dialysis liquid and on the other hand with used liquid.

The connector 46 placed on the injection line 43 for injecting disinfection liquid is open, and the line section integral with the reservoir 40 is connected to a source of concentrated disinfection liquid. The reservoir 40 is filled with disinfection liquid to the upper level 41 by means of the pump 44, then the injection line 43 is connected once again to the supply line 1.

The method for filling the hydraulic circuit with a disinfection liquid is then started up by the control unit 31 according to a pre-established program comprising several phases corresponding to the simultaneous emptying and filling of different portions of the circuit. During this entire method, the scavenging pump 19 and the pump 44 for disinfection liquid are functioning continuously. The delivery rate of the latter is adjusted so that the mixture (first liquid or bactericidal liquid) of water and concentrated disinfection liquid which forms at the junction of the supply line 1 and the injection line 43 is bactericidal. By way of example, if the concentrated disinfection liquid chosen is Javelle water at 48° chlorometric, the delivery rate of the injection pump 44 for this liquid will be chosen in such a way that the dilution ratio is approximately 30.

In the description of the phases of the disinfection method which follows, the pumps which are not mentioned are not functioning and they act as occlusion members. Unless otherwise indicated, the valve 18 arranged on the purge line 17 is closed.

First phase

The valve 18 is open and the injection pumps 6a, 6b of the dialysis liquid generator are functioning. The duration of this phase is calculated in such a way that, taking account of the delivery rate of the pumps 6a, 6b and 13, the dialysis liquid generator, the first chamber 9 of the first filter 8, the recirculation line 12 and the purge line 17 are filled completely with bactericidal liquid at the end of the first phase. The pumps 6a and 6b are then stopped and the valve 18 is closed.

Second phase

The second circulation pump 20 is functioning. The three-way valve 34 is arranged so as not to obstruct the removal line 2. The duration of this phase is calculated so that, taking into account the delivery rate of the pump 20, the second filter 21 and the lines 25, 26 which are connected to it, the loop line 27, the removal line 2, the junction line 3, and the portion of the supply line 1 included between the loop line 27 and the junction line 3, are completely filled with bactericidal liquid at the end of the second phase. The circulation pump 20 is then stopped.

Third phase

The first circulation pump 19 is functioning and the three-way valves 33, 34 are arranged in such a way as to permit the circulation of the liquid in the calibration line 32. The duration of this phase is calculated so that, taking into account the delivery rate of the pump 19, the calibration line 32 is completely filled with bactericidal liquid at the end of the third phase. The circulation pump 19 is then stopped and the three-way valve 34 is arranged in such a way as to re-establish the passage in the removal line 2.

Fourth phase

The second circulation pump 20 and the ultra-filtration pump 35 are functioning. The valve 37 of the device for measuring the ultrafiltration flow rate is open until the branch line 36 is filled with bactericidal liquid. The valve 37 is then closed in such a way that the burette 38 fills. The duration of this phase is calculated so that, taking into account the delivery rate of the ultrafiltration pump 35, the branch line 36 and the burette 38 are completely filled with bactericidal liquid at the end of this fourth phase.

When the hydraulic circuit of the dialysis machine is completely filled with bactericidal liquid, as has just been described, all the pumps are stopped for a defined period of time running from the end of the first phase. During this period, which, taking the example of disinfectant mentioned above, is preferably of the order of 30 minutes, the first liquid stagnates in the circuit and exerts its bactericidal action. This duration is, however, much too short for the circuit to suffer any corrosion.

In accordance with the invention, the initial volume of concentrated disinfection liquid introduced into the reservoir 40 is chosen so that at the end of the filling of the hydraulic circuit, a defined residual volume of concentrated disinfection liquid remains in the reservoir 40.

During the period of stagnation, the connector 46 of the injection line 43 for injecting disinfection liquid is open, and the line portion integral with the reservoir 40 is connected to a source of water. The reservoir 40 is filled by means of the pump 44 up to the level of the upper level detector 41, and then the line 43 is reconnected to the supply line 1. The reservoir 40 then contains a second diluted disinfection liquid.

In accordance with the invention, at the end of the period of stagnation, the hydraulic circuit is emptied completely of the first disinfection liquid, and it is filled again, in accordance with the fourphase program described above, by means of a third liquid (or bacteriostatic liquid) resulting from a metered mixing of water and of the second disinfection liquid prepared in the reservoir 40 during the stagnation period. The dilution ratio is chosen in such a way that the third liquid is bacteriostatic and has no corrosive action on the circuit, even after a stagnation of several hours, preferably at least twelve hours. To return to the example of Javelle water at 48° chlorometric given hereinabove, the desired result is obtained by choosing, for the second liquid prepared in the reservoir 40 during the stagnation period, a dilution ratio of water to concentrated disinfection solution of approximately 3.5 and by adjusting the injection pump 44 for disinfection liquid in such a way that, during the filling of the hydraulic circuit with the bacteriostatic liquid, the dilution ratio of water to second liquid is approximately 30.

According to an alternative embodiment of the invention, the concentrated disinfection liquid is prepared from a defined volume of water in which a defined quantity of soluble disinfectant in the form of powder, granules or, preferably, tablets, is dissolved. The reservoir 40 then comprises an orifice for the introduction of the soluble disinfectant. The preparation of the concentrated disinfection liquid and of the second liquid which are used, respectively, to prepare the bactericidal liquid and the bacteriostatic liquid is then slightly different from what has been described above, in that the reservoir 40 in both cases is filled by means of water circulated in the supply line 1.

In the above description, the reservoir 40 equipped with the upper level and lower level detectors 41 and 42 has been depicted as an integral part of the machine. It is of course possible to use a container which is external to the machine and which would be provided to the user with a defined volume of concentrated disinfection liquid corresponding to the upper level of the reservoir 40.

The invention is not limited to the specific embodiments which have just been described and is open to variations.

We claim:

1. Method for disinfection of the hydraulic circuit of a dialysis machine, comprising an inlet for connection to an external water source and a plurality of open lines intended to be connected, in an operational configuration of the machine, to different consumable accessories, comprising the steps of:

closing the open lines on the hydraulic circuit in such a way as to form a closed network of lines;

bringing a reservoir containing a concentrated disinfection liquid into communication with the hydraulic circuit, in proximity to the inlet;

instigating a proportional flow of water and of concentrated disinfection liquid in the hydraulic circuit in such a way as to produce a first liquid having a bactericidal action;

interrupting the flow of water and of concentrated disinfection liquid when the hydraulic circuit is filled with bactericidal liquid, the initial volume of concentrated disinfection liquid in the reservoir being chosen such that at the end of the filling of the hydraulic circuit, a residual volume remains in the reservoir;

adding a volume of water to the residual volume in the reservoir in order to produce a second liquid;

emptying the hydraulic circuit of the bactericidal liquid;

instigating simultaneously a proportional flow of water and of the second liquid in the hydraulic circuit in such a way as to produce a third liquid having a bacteriostatic action and capable of remaining in the hydraulic circuit for at least twelve hours without causing corrosion there;

filling the hydraulic circuit with bacteriostatic liquid.

2. Method according to claim 1, wherein prior to the step of bringing the reservoir into communication with the hydraulic circuit, it comprises the step of filling the reservoir with a defined volume of concentrated disinfection liquid.

3. Method according to claim 2, wherein the reservoir is filled to a predetermined upper level with the concentrated disinfection liquid.

4. Method according to claim 1, wherein prior to the step of bringing the reservoir into communication with the hydraulic circuit, it comprises the step of filling the reservoir with a defined volume of water and of introducing thereto a defined quantity of soluble disinfectant in the form of a powder, granules or tablets.

5. Method according to claim 4, for a hydraulic circuit comprising a first filter intended for the filtration of a dialysis liquid, wherein a second filling phase comprises the filling of the first filter.

6. Method according to claim 5, for a hydraulic circuit comprising a second filter intended for the filtration of a perfusion liquid, wherein a third filling phase comprises the filling of the second filter.

7. Method according to claim 6, for a hydraulic circuit comprising an extraction device for extracting a liquid from a section of the circuit intended to be connected, in an operational configuration of the machine, to a dialyser, wherein a fourth filling phase comprises the filling of the extraction device.

8. Method according to claim 1, wherein the step of filling the hydraulic circuit with the bactericidal liquid and the step of filling the hydraulic circuit with the bacteriostatic liquid are performed in several phases corresponding to the filling of several portions of the hydraulic circuit.

9. Method according to claim 8, for a hydraulic circuit comprising a dialysis liquid generator, wherein a first filling phase comprises the filling of the dialysis liquid generator.

10. Method according to claim 8, for a hydraulic circuit comprising a first filter intended for the filtration of a dialysis liquid, wherein a second filling phase comprises the filling of the first filter.

11. Method according to claim 10, wherein the stagnation step lasts about 30 minutes.

12. Method according to claim 1, wherein the emptying of the bactericidal liquid is instigated by the filling of the hydraulic circuit with the bacteriostatic liquid.

13. Method according to claim 1, wherein the step of filling the hydraulic circuit with the bacteriostatic liquid is preceded by a step involving stagnation of the bactericidal liquid in the circuit.

14. Method according to claim 1, wherein
   the concentrated disinfection liquid is Javelle water at 48° chlorometric,
   a dilution ratio of water in the first or bactericidal liquid to the concentrated disinfection liquid is approximately 30,
   a dilution ratio of water in the second liquid to the concentrated disinfection liquid is approximately 3.5, and
   a dilution ratio of water in the third or bacteriostatic liquid to the second liquid is approximately 30.

* * * * *